United States Patent [19]

Takagi

[11] Patent Number: 5,782,969
[45] Date of Patent: Jul. 21, 1998

[54] IONIC SPIROPYRAN AND PHOTOCHROMIC CLAY CONJUGATE COMPRISING THE SAME

[75] Inventor: Katsuhiko Takagi, Aichi-ken, Japan

[73] Assignee: Nissho Iwai Bentonite Co., Ltd., Tokyo, Japan

[21] Appl. No.: 617,573

[22] Filed: Mar. 19, 1996

[30] Foreign Application Priority Data

Apr. 20, 1995 [JP] Japan .................. 7-117703

[51] Int. Cl.$^6$ .................. C08K 5/00
[52] U.S. Cl. .................. 106/498; 106/487; 252/586; 252/589; 430/345; 548/409
[58] Field of Search .................. 430/345; 252/586, 252/589; 548/409; 106/487, 498

[56] References Cited

U.S. PATENT DOCUMENTS

| | | | |
|---|---|---|---|
| 3,293,055 | 12/1966 | Baum | 428/403 |
| 3,999,989 | 12/1976 | Ono et al. | 548/409 |
| 5,252,437 | 10/1993 | Suzuki et al. | 430/345 |
| 5,426,018 | 6/1995 | Hibino et al. | 430/345 |
| 5,474,715 | 12/1995 | Tagaya et al. | 252/586 |
| 5,581,090 | 12/1996 | Goudjil | 250/474.1 |

OTHER PUBLICATIONS

Chemical Abstract 114:111676 of J. Chem. Soc., Faraday Trans., 86 (21), 3616–21, Dec. 1990.
Japanese Patent Office Abstract, JP 02-264246, vol. 16, No. 20, Jan. 1991.
Macromolecules, vol. 20, No. 11, pp. 2958–2959 (1987) (American Chemical Society). (no month avail.).
Macromolecules, vol. 23, No. 1, pp. 31–35 (1990) (American Chemical Society). (no month avail.).

*Primary Examiner*—Mark L. Bell
*Assistant Examiner*—Scott L. Hertzog
*Attorney, Agent, or Firm*—Jacobson, Price, Holman & Stern, PLLC

[57] ABSTRACT

Present invention provides ionic spiropyran compounds having a C10–C22 alkyl group or groups at the 1'- and/or 8-positions of 3',3'-dimethyl-6-nitrospiro[2H-1-benzopyran-2',2'-indoline] and a composite material made by conjugating the said ionic spiropyrans with clay mineral, the said composite material being capable of forming a transparent thin film which is photo-interconvertible between the said spiropyrans and the corresponding merocyanines.

13 Claims, No Drawings

IONIC SPIROPYRAN AND PHOTOCHROMIC CLAY CONJUGATE COMPRISING THE SAME

The present invention relates to surface-active type spiropyran compounds which have an alkyl group containing at least 10 carbon atoms and an ionic substituent and which are typical ones among well-known photochromic compound interconvertible between spiropyrans (colorless) and merocyanines (colored) upon lighting or heating.

The present invention relates further to photochromic composite materials conjugated with clay adsorbed the said spiropyran compounds into openings of clay layers and the composite materials are capable of forming a transparent thin film being photo-interconvertible between the said spiropyrans and the corresponding merocyanines.

Spiropyran compounds having photochromic character are new substances attracting attention in the photonic field and are used as photo-recording material, displaying material, nonlinear optical material and the like.

Spiropyran compounds having such photo-functionality have been known for a long time and their derivatives having a variety of substituent groups have been synthesized. The introduction of a substituent group generally gives rise to the color change of colored material. However, a surface-active type compound having a long-chain alkyl group and an ionic substituent, for the purpose of dispersing or orienting in carrier material, is not known.

The hydrophobic spiropyran compounds substituted with a non-ionic long-chain alkyl group have been synthesized. Although there is a precedent that spiropyran compounds without such substituent have been dispersed or oriented in hydrophobic polymer, they have no ionic substituent and differ fundamentally from the surface-active type spiropyran compounds according to the invention as regards a method for dispersing or orienting.

Interconversion between spiropyrans and merocyanines by application of a wide range of light or heat is well known.

For this reason various methods for preparing a recording material due to a photon or heat mode have been studied.

The most difficult problem in this case exists in the gradual vanishment of a record due to the isomerization from merocyanines to spiropyrans which may occur in the dark or below a threshold temperature. Therefore, it is desirable that the spiropyran derivatives are stable to light and prolonged heating and their composite materials conjugated with carrier materials are suitable as a formative substance. In order to prevent thermal isomerization the skeletal modification of spiropyran structure and/or the introduction of a substituent group as well as the selection of a medium is carried out. Where an improved compound is incorporated into a polymer matrix or Langmuir-Brodgett film, the thermal stability of the composite material may be increased.

The increased thermal stability of a merocyanine compound, which is incorporated into a polymer matrix or Langmuir-Brodgett film, is due to the aggregation state of merocyanine molecules oriented regularly in a medium. On the other hand, stratified clay mineral, which is an important material of the invention, is capable of incorporating an ionic guest organic material into openings of the clay layers to form a regularly oriented aggregate. Therefore it is important to substitute the merocyanine compound with a long-chain alkyl groups and/or to introduce an ionic substituent group capable of causing adsorption. Alternatively, where the spiropyran compound has an electric charge opposite to that of the interface of clay, electrostatic interaction between the spiropyran compound and the interface of clay is expected. An amount of the spiropyran compound adsorbed on the ionic interface is proportionate to the electric charge density of the interface.

However, the non-ionic spiropyran compounds known heretofore reveal an extremely low adsorption coefficient and, even if they were adsorbed, are converted to a colored form. Therefore the desired photo-functionality could not be obtained.

In order to solve the problems described above there have been synthesized the spiropyran compounds having both a long-chain alkyl group and an ionic substituent. The spiropyrans possess the property of photochromism interconvertible between spiropyrans (colorless) and merocyanines (colored) upon lighting or heating. Photochromic materials are also prepared by adsorbing the said spiropyran compounds into openings of clay layers, followed by conjugating with the clay which is capable of forming a transparent thin film being photo-interconvertible between the said spiropyrans and the corresponding merocyanines.

The surface-active type spiropyran compounds of the invention are conjugated with a stratified inorganic compound prepared from 2:1 type cation-exchange clay such as smectite or anion-exchange clay magnesia octahedral sheets such as hydrotalcite. Alternatively, they are conjugated with Langmuir-Brodgett type lipid bilayer, multilayer thin film, polymer-electrolyte film or the like prepared on various types of basic plates under investigation in order to acquire the physical properties suitable for dispersing or orienting.

The surface-active type spiropyran compounds of the invention have both a hydrophobic alkyl group and an ionic substituent in the molecule and can be arranged in regular sequence on the basis of hydrophobicity and electrostatic interaction with a carrier material.

The spiropyran compounds (1a) and (1f) listed in Table 1 among the spiropyran compounds incorporated into monmorillonite cation-exchange clay and magnesium oxide anion-exchange clay respectively reveal inverse photochromism in the film, that is, fading in light and coloring in dark. This character can be converted to normal photochromism if, after completion of 10% of adsorption, remaining ionic sites are substituted by an ionic surfactant in order to give rise to hydrophobicity. The spiropyran compounds discussed below in Table 1 are based on the following structural formula:

TABLE 1

| spiropyran | R¹ | R² | R³ | R⁴ |
|---|---|---|---|---|
| 1a | $CH_3$ | $CH_2-{}^+N\text{(pyridinium)}$ | $NO_2$ | H |
| 1b | $CH_3$ | H | $CH_2-{}^+N\text{(pyridinium)}$ | H |
| 1c | $C_{18}H_{37}$ | $CH_2-{}^+N\text{(pyridinium)}$ | $NO_2$ | H |
| 1d | $(CH_2)_{10}-{}^+N\text{(pyridinium)}$ | H | $NO_2$ | H |
| 1e | $(CH_2)_{10}-{}^+N\text{(pyridinium)}$ | $CH_2OCOC_{18}H_{37}$ | $NO_2$ | H |
| 1f | $CH_3$ | H | $CO_2$ | H |
| 1g | $CH_3$ | H | $NO_2$ | $CO_2$ |
| 1h | $CH_3$ | H | $NO_2$ | $CH_2-{}^+N\text{(pyridinium)}$ |

The invention is further illustrated by the following Examples, of which Examples 1 to 4 illustrate the preparation of various ionic spiropyran compounds and Examples 5 to 7 illustrate the preparation of various photochromic materials conjugated with clay.

(1) Ionic spiropyran compounds:

EXAMPLE 1

Spiropyran compound (1b)

(a) 6-Chloromethyl-1',3',3'-trimethylspiro[2H-1-benzopyran-2,2'-indoline]

A solution of 1.6 g (9.3 mmol) of 1,3,3-trimethyl-2-methyleneindoline and 1.6 g (9.3 mmol) of 5-chloromethylsalicylaldehyde dissolved in 100 ml of benzene was heated under reflux for 2 hours in a reaction vessel provided with a Soxlet extractor, in which anhydrous magnesium sulfate was packed in a cylindrical filter paper. After completion of the reaction, the solvent was distilled off under reduced pressure to give crude product. This product was purified by gel permeation chromatography through a column (30 cm length) packed with polystyrene beads (a product of Nihon Bunseki Kogyo Co.: JAIGEL-2H) to give the title compound in a pure state.

NMR (δ), (CDCl3): 6.8–7.2 (7H, m), 6.5 (1H, d), 5.7 (1H, d), 4.6 (2H, s), 2.8 (3H, s), 1.3 (3H, s), 1.2 (3H,s).

(b) Spiropyran compound (1b)

To a solution of 0.54 g of the powdery indoline compound prepared above in 50 ml of ethanol were added 10 ml of pyridine, and the resulting mixture was heated under reflux for 24 hours. Precipitates deposited were collected by filtration to give 0.65 g of the desired compound as organge-crystals in a 94.5% yield.

EXAMPLE 2

Spiropyran compound (1c)

(a) 3,3-Dimethyl-2-methylene-1-octadecylindoline

A mixture of 5.2 g (32 mmol) of 2,3,3-trimethylindoline and 15.8 g (48 mmol) of octadecylammonium bromide was heated with stirring followed by treating with a solution of 8 g of sodium hydroxide in 50 ml of water. After usual working-up, there were obtained 4.2 g of the title compound in a 84.1% yield.

(b) Spiropyran compound (1c)

To a solution of 1.05 g (4.87 mmol) of 3-chloromethyl-2-hydroxy-5-nitrobenzaldehyde in 100 ml of benzene were added 2.0 g (4.9 mmol) of the octadecylindoline compound prepared above, and the resulting mixture was heated under reflux for 5 hours in the presence of anhydrous magnesium sulfate. After cooling, the reaction mixture was purified by column chromatography through silica gel using a 80:20 mixture of benzene and ethyl acetate as an eluent to give 1.03 g of the desired product having m.p. 159°–161° C. in a 34.8% yield. This product was dissolved in 20 ml of pyridine and the solution was heated under reflux for 72 hours. After completion of the reaction, the reaction mixture was worked-up as usual to give the title compound as a powder.

EXAMPLE 3

Spiropyran compound (1d)

(a) 1'-(ω-Bromodecyl)-3',3'-dimethyl-6-nitrospiro[2H-1-benzo-pyran-2,2'-indoline]

A mixture of 1.55 g (9.3 mmol) of 5-nitro-2-hydroxybenzaldehyde and 3.52 g (9.3 mmol) of 1-(ω-bromodecyl)-3,3-dimethyl-2-methyleneindoline, prepared previously by reacting 2,3,3-trimethylindoline with 1,10-dibromodecane, was heated in 2-butanone for 5 hours. After completion of the reaction, the reaction mixture was concentrated under reduced pressure. The concentrate was purified by column chromatography through silica gel using a 80:20 mixture of benzene and hexane as an eluent to give 1.48 g of the title compound in a 30% yield.

(b) Spiropyran compound (1d)

To a solution of the indoline compound prepared above in chloroform were added 20 ml of pyridine, and the resulting mixture was heated under reflux for 72 hours. The reaction mixture was worked-up as usual to give 0.82 g of the desired quaternary pyridinium compound in a 48% yield.

NMR (δ), (CDCl3): 9.5 (1H, m), 8.5 (2H, m), 8.1 (1H, m), 7.9 (1H, m), 7.2–6.5 (7H, m), 6.5 (1H, d, J=7 Hz), 5.8 (2H, d, J=12 Hz), 5.0 (1H, s), 3.1 (3H, m), 1.2 (18H, s).

EXAMPLE 4

Spiropyran compound (1e)

(a) 1'-(ω-Bromodecyl)-8-(docosanoyloxy)methyl-3',3'-dimethyl-6-nitrospiro[2H-1-benzopyran-2,2'-indoline]

Following the procedure described above, but using 1.82 g (4.81 mmol) of 1-(ω-bromodecyl)-3,3-dimethyl-2-methyleneindoline and 2.52 g (4.78 mmol) of 3-[(docosanoyloxy)-methyl]-2-hydroxy-5-nitrobenzaldehyde, there were obtained 1.63 g of the title compound in a 38.4% yield.

(b) Spiropyran compound (1e)

A mixture of 20 ml of pyridine and 20 ml of chloroform was added to 1.63 g (1.84 mmol) of the indoline compound prepared above and the resulting mixture was worked-up as usual. The crude product was purified by gel permeation chromatography through a column (30 cm-length) packed with polystyrene beads (a product of Nihon Bunseki Kogyo Co.: JAIGEL-2H) using a 80:20 mixture of benzene and hexane as an eluent to give 0.85 g of the title compound in a 48.2% yield.

NMR (δ), (CDCl3): 8.9 (1H, s), 8.7 (2H, m), 8.3 (1H, t), 8.1 (1H, s), 7.7 (2H, m), 7.3 (2H, m), 7.0 (3H, m), 6.5 (1H, d), 6.3 (1H, d), 5.9 (2H, m), 3.4 (2H, t), 3.1 (2H, m), 2.49 (3H, s), 1.8 (4H, m), 1.2 (15H, m), 1.0 (3H, s).

Owing to the fact that the spiropyran compounds are charged reversely to the electrostatic charge of the interface of the clay mineral described below, a quaternary salt of pyridine or amine as a cationic substituent and a carboxylic acid group as an anionic substituent were used.

(2) Photochromic materials conjugated with clay:

EXAMPLE 5

To a mixture of a 1×10-4M aqueous solution of a spiropyran compound (1a–e,f) and 5 meq of an aqueous dispersion of monmorillonite cation-exchange clay in the mole ratio of 0.1:1 was applied ultrasonic, and the resulting mixture was stirred at room temperature (20° C.) for an hour. The aqueous dispersion thus obtained was casted on a glass slide and allowed to stand to give a semitransparent film having arbitrary thickness.

The aqueous dispersion was separated by filtration through a membrane filter followed by drying overnight at room temperature in a vacuum to produce an orange powder.

EXAMPLE 6

A mixture of a 1×10$^{-4}$M solution of a spiropyran compound (1a–e, h) and a 9×10$^{-4}$M solution of cetyltrimethylammonium bromide and 5 meq of an aqueous dispersion of monmorillonite cation-exchange clay were mixed in the mole ratio of 1:1. To the mixture was applied ultrasonic, and the resulting mixture was stirred at room temperature (20° C.) for an hour. The aqueous dispersion thus obtained was separated by filtration through a membrane filter followed by drying overnight at room temperature in a vacuum to produce an orange powder. A solution of the powder dissolved in decanol or benzene was concentrated and adjusted to be 1×10$^{-4}$M. To the solution was applied ultrasonic, and the resulting solution was stirred on a magnetic stirrer overnight at room temperature. Following the casting procedure described above, there was obtained the desired film.

EXAMPLE 7

A 1×10$^{-4}$M aqueous solution of a spiropyran compound (1f, g) and 5 meq of an aqueous dispersion of magnesium oxide anion-exchange clay were mixed in the mole ratio 1:1. To the mixture was applied ultrasonic, and the resulting mixture was stirred on a magnetic stirrer at room temperature (20° C.) for an hour. By casting the aqueous dispersion analogously, there was obtained the desired film.

The spiropyran compounds incorporated into the photochromic material have primarily an ionic substituent. That is, they have a pyridinium group as a cation substituent in cation-exchange clay or a carboxylic acid as an anion substituent in anion-exchange clay. The spiropyran compound is mixed with a clay dispersion and the mixture is stirred overnight at 50° C. followed by filtration and drying to produce a white powder or to form a film by a casting method.

In the photochromic material conjugated with clay thus obtained, the thermal stability of merocyanines was markedly improved. The material interconvertible between colorless spiropyrans and red merocyanines by irradiation of ultraviolet and visible rays may be used as that having memory and recording functions by means of photon mode. In general, as machine-made papers are processed by surface finishing by using clay such as kaolin, the application of the complex clay material of the invention to the surface of paper may invest the paper with writing function by irradiation of ultraviolet rays and eliminating function by irradiation of visible rays.

The spiropyrans incorporated into montmorillonite cation-exchange clay and the spiropyrans incorporated into magnesium oxide anion-exchange clay in the form of film reveal inverse photochromism, that is, fading in light and coloring in dark. However these compounds have characteristics making them capable of converting to normal photochromism if, after completion of 10% of adsorption, the remaining ionic site is substituted by an ionic surfactant in order to give rise to hydrophobicity. In the film prepared from monmorillonite cation-exchange clay, in which the spiropyrans having a cationic substituent in the 1'-position and a long-chain alkyl substituent in the 8-position are incorporated, the thermal stability is ten thousand or more times as compared with that in a solution and both coloring and fading processes proceed more rapidly by irradiation of visible and ultraviolet rays respectively.

The surface-active type spiropyran compounds of the invention are conjugated with the stratified inorganic compound prepared from 2:1 type cation-exchange clay represented by smectite or anion-exchange clay magnesia octahedral sheets represented by hydrotalcite or with a carrier material such as Langmuir-Brodgett type lipid bilayer, multilayer thin film, polymer-elctrolyte film or the like prepared on various types of basic plates under investigation to afford ionic spiropyran compounds having increased adsorbable strength and physical properties suitable for dispersing and/or orienting.

Conjugation of spiropyran compounds with clay mineral gives rise to a composite material which is capable of forming thin films and has remarkable thermal stability.

The spiropyran compounds incorporated into monmorillonite cation-exchange clay or magnesium oxide anion-exchange clay reveal inverse photochromism in the form of film, that is, fading in light and coloring in dark. However after completion of 10% of adsorption, these compounds may readily be converted to hydrophobic compounds having normal photochromism by substituting the remaining ion site with an ionic surfactant.

In the film prepared from monmorillonite cation-exchange clay into which a spiropyran compound (1e) is incorporated, the thermal stability is ten thousand or more times as compared with that in solution and both coloring and fading processes proceed more rapidly by irradiation of visible and ultraviolet rays.

Where the photochromic composite materials of the invention are used in the surface finishing of paper-manufacturing process, they are effective for practical application in manufacturing photo-recording paper.

What is claimed is:

1. Ionic spiropyran compound having a long chain alkyl group or groups of at least 10 carbon atoms at the 1'- or 8-positions of 3', 3'-dimethyl-6-nitrospiro.

2. A photochromic material or materials conjugated with clay comprising a red-colored merocyanine derived from an ionic spiropyran of claim 1 wherein the thermal stability of said red colored mercyanine in light is improved by absorbing said ionic spiropyran compound into a cationic substituent on the surface of 2:1 type cation-exchange clay.

3. The photochromic material or materials of claim 2 wherein the cation-exchange clay is smectite.

4. The photochromic material or materials of claim 2 wherein the ionic substituent is located at the 1'-, 5', or 8-position of the spiropyran compound.

5. A photochromic material or materials conjugated with clay comprising a red-colored merocyanine derived from an ionic spiropyran of claim 1 wherein the thermal stability of said red colored merocyanine in light is improved by absorbing said ionic spiropyran compound having an anionic substituent on the surface of anion-exchange clay consisting of magnesium octahedral sheets.

6. The photochromic material or materials of claim 5 wherein the anion-exchange clay is hydrotalcite.

7. The photochromic material or materials of claim 5 wherein the ionic substituent is located at the 1'-, 5', or 8-position of the spiropyran compound.

8. A conjugate comprising an ionic spiropyran compound of claim 1 and clay wherein said spiropyran compound is incorporated into the clay and has a long chain alkyl group or groups of at least 10 carbon atoms and the clay is selected from the group consisting of magnesium oxide anion-exchange clay and monmorillonite cation-exchange clay.

9. The ionic spiropyran compound of claim 1 wherein the ionic substituent is at the 8- position.

10. The ionic spiropyran compound of claim 1 wherein the alkyl group is at the 1'- position.

11. The ionic spiropyran compound of claim 1 wherein the alkyl group is at the 8- position.

12. The ionic spiropyran compound of claim 1 wherein the ionic substituent is at the 1'- position.

13. The ionic spiropyran compound of claim 1 wherein the ionic substituent is at the 5'- position.

* * * * *